United States Patent
Alig et al.

(10) Patent No.: US 6,642,386 B2
(45) Date of Patent: Nov. 4, 2003

(54) N-(4-CARBAMIMIDOYL-PHENYL)-GLYCINE DERIVATIVES

(75) Inventors: Leo Alig, Magden (CH); Katrin Groebke Zbinden, Basel (CH); Ulrike Obst, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/350,617

(22) Filed: Jan. 24, 2003

(65) Prior Publication Data

US 2003/0166683 A1 Sep. 4, 2003

(30) Foreign Application Priority Data

Feb. 6, 2002 (EP) .............................. 02002009

(51) Int. Cl.$^7$ ...................... C07D 211/40; C07D 211/10
(52) U.S. Cl. ...................... 546/216; 546/230; 546/231; 546/235
(58) Field of Search ................. 546/216, 230, 546/231, 235

(56) References Cited

FOREIGN PATENT DOCUMENTS

| WO | WO 00/35858 | 12/1999 |
| WO | WO 01 90051 | 11/2001 |

*Primary Examiner*—Charanjit S. Aulakh
(74) *Attorney, Agent, or Firm*—George W. Johnston; John P. Parise

(57) ABSTRACT

The invention is concerned with water soluble N-(4-carbamimidoyl-phenyl)-glycine derivatives of formula (I)

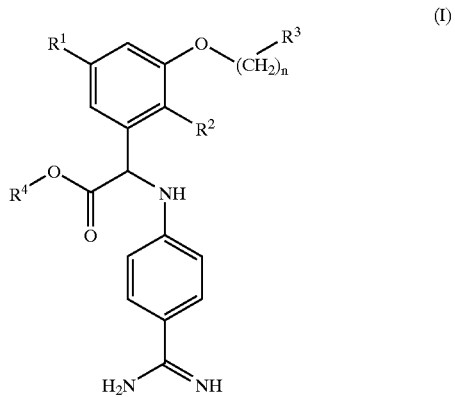

wherein $R^1$ to $R^4$ and n are as defined in the description and in the claims, as well as physiologically acceptable salts thereof. These compounds inhibit the formation of coagulation factors Xa, IXa and thrombin induced by factor VIIa and tissue factor and can be used as medicaments.

39 Claims, No Drawings

N-(4-CARBAMIMIDOYL-PHENYL)-GLYCINE DERIVATIVES

BACKGROUND OF THE INVENTION

1. Field

The invention is concerned with novel water soluble N-(4-carbamimidoyl-phenyl)-glycine derivatives.

2. Description

Inhibitors of factor VIIa have been suggested for the inhibition of the formation of thrombi and for the treatment of related diseases (WO 00/35858). Unfortunately, the compounds disclosed in WO 00/35858 have lower than desirable solubility in water and are not particularly suitable for subcutaneous applications.

Accordingly, there is a long felt need in the art for factor VIIa inhibitors that have increased water solubility and enhanced inhibitory activity.

SUMMARY OF THE INVENTION

The subject invention provides compounds of the formula:

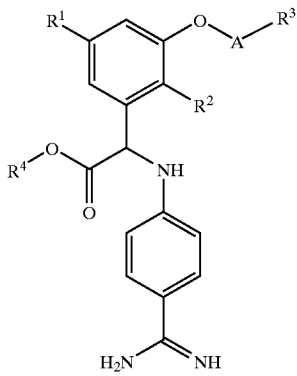

(I)

wherein
- $R^1$ is lower-alkoxy;
- $R^2$ is halogen;
- $R^3$ is piperidinyl or piperidinyl substituted with lower-alkyl, hydroxy-lower-alkyl, carboxy-lower-alkyl or lower-alkoxy-carbonyl-lower-alkyl;
- $R^4$ is hydrogen or lower-alkyl;
- A is —(CH$_2$)$_n$— or —(CH$_2$)$_n$— which is substituted with lower-alkyl; and
- n is 0 to 3. Pharmaceutically acceptable salts of these compounds are also an aspect of this invention.

Certain preferred compounds are where $R^1$ is ethoxy, $R^2$ is fluorine, and $R^3$ is piperidinyl or piperidinyl substituted with methyl or hydroxy-ethyl, such as 1-methyl-piperidin-3-yl; 1-(2-hydroxy-ethyl)-piperidin-4-yl; 1-(2-hydroxy-ethyl)-piperidin-3-yl; piperidin-4-yl; or 1-methyl-piperidin-4-yl. $R^4$ is favorably hydrogen or ethyl, and especially hydrogen. It is preferred where n is 0 to 2, and favorably n is 0.

A preferred group of compounds are of the formula

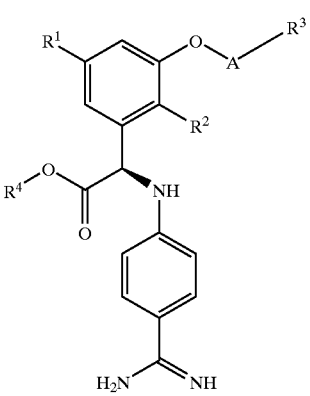

(Ia)

wherein $R^1$, $R^2$, $R^3$, $R^4$, A, and n have the significances given above. As above, pharmaceutically acceptable salts of these compounds are also an aspect of this invention.

Other useful compounds are of the formula:

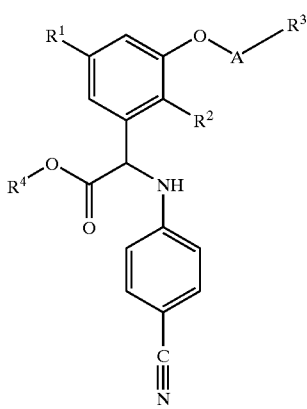

(II)

wherein $R^1$, $R^2$, $R^3$, $R^4$, A, and n have the significances given above. Pharmaceutically acceptable salt of these compounds are also an aspect of the invention.

DETAILED DESCRIPTION OF THE PREFERRED EMBODIMENTS

The subject invention will now be described in terms of its preferred embodiments. These embodiments are set forth to aid in understanding the invention but are not to be construed as limiting the invention in any way.

The invention is concerned with water soluble N-(4-carbamimidoyl-phenyl)-glycine derivatives of the formula (I)

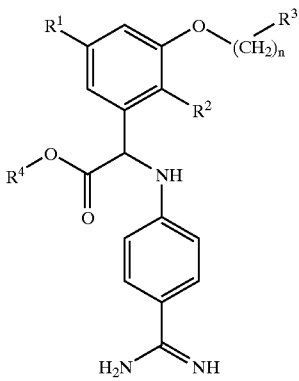

(I)

wherein
- $R^1$ is lower-alkoxy,
- $R^2$ is halogen,
- $R^3$ is piperidinyl optionally substituted with lower-alkyl, hydroxy-lower-alkyl, carboxy-lower-alkyl or lower-alkoxy-carbonyl-lower-alkyl,
- $R^4$ is hydrogen or lower-alkyl,
- n is 0 to 3, and the —$(CH_2)_n$— group can optionally be substituted with lower-alkyl, and pharmaceutically acceptable salts thereof.

Further, the invention is concerned with a process for the manufacture of the above compounds, pharmaceutical preparations which contain such compounds as well as the use of these compounds for the production of pharmaceutical preparations.

The compounds of formula (I) are active compounds and inhibit the formation of coagulation factors Xa, Ixa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumor cells and prevent metastases. They can therefore also be used as antitumor agents.

Inhibitors of factor VIIa had previously been suggested for the inhibition of the formation of thrombi and for the treatment of related diseases (WO 00/35858). However, there is still a need for factor VIIa inhibitors which exhibit a much higher solubility in water in order to be suitable for subcutaneous applications and which at the same time exhibit a higher inhibitory activity.

The present invention provides compounds of formula (I) which are factor VIIa inhibitors and unexpectedly exhibit the desired increased water solubility and increased inhibitory activity compared to the compounds known from WO 00/35858. These inventive compounds further exhibit improved pharmacological properties compared to the known compounds.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "alkoxy" refers to the group R'—O—, wherein R' is an alkyl. The term "lower-alkoxy" refers to the group R'—O—, wherein R' is a lower-alkyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulfuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) can further form salts with bases. Examples of such salts are alkaline, earth-alkaline and ammonium salts such as e.g. Na-, K-, Ca- and Trimethylammonium salt. The term "pharmaceutically acceptable salts" also refers to such salts.

In detail, the present invention relates to compounds of formula (I)

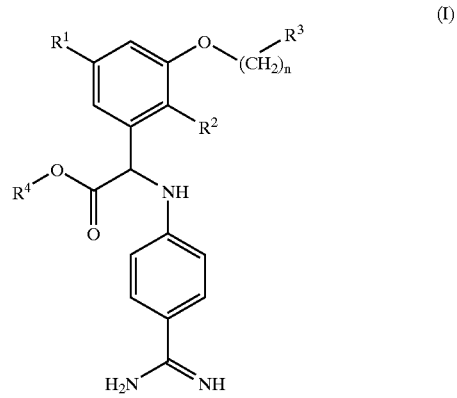

(I)

wherein
- $R^1$ is lower-alkoxy,
- $R^2$ is halogen,
- $R^3$ is piperidinyl optionally substituted with lower-alkyl, hydroxy-lower-alkyl, carboxy-lower-alkyl or lower-alkoxy-carbonyl-lower-alkyl,
- $R^4$ is hydrogen or lower-alkyl,
- n is 0 to 3, and the —$(CH_2)_n$— group can optionally be substituted with lower-alkyl, and pharmaceutically acceptable salts thereof.

The compounds of formula (I) have at least,one asymmetric C atom and can therefore exist as an enantiomeric mixture, diastereomeric mixture or as optically pure compounds. Compounds of formula (I) can exist in tautomeric forms and the invention encompasses all such tautomeric forms.

Compounds of formula (I) are individually preferred and physiologically acceptable salts thereof are individually preferred, with the compounds of formula (I) being particularly preferred.

Preferred compounds of formula (I) are those, wherein $R^1$ is ethoxy. Another preferred embodiment of the present invention relates to compounds as described above, wherein $R^2$ is fluorine.

In a further preferred embodiment the invention relates to compounds as described above in which $R^3$ is piperidinyl optionally substituted with methyl or hydroxy-ethyl. Compounds in which $R^3$ is 1-methyl-piperidin-3-yl, 1-(2-hydroxy-ethyl)-piperidin-4-yl, 1-(2-hydroxy-ethyl)-piperidin-3-yl, piperidin-4-yl or 1-methyl-piperidin-4-yl are more preferred.

The invention embraces especially compounds in accordance with the above definitions in which $R^4$ is hydrogen or ethyl, with those wherein $R^4$ is hydrogen being more preferred.

Moreover, the invention relates especially to compounds as defined above in which n is 0–2, with those wherein n is 0 being particularly preferred.

Of the compounds of formula (I) as described above, the R-enantiomers are preferred. Such R-enantiomers are characterised by formula (Ia). Therefore compounds according to the definitions given above characterised by formula (Ia)

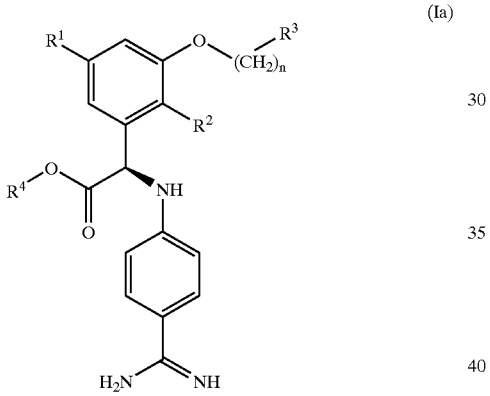

(Ia)

wherein $R^1$, $R^2$, $R^3$, $R^4$ and n have the significances given above, are also preferred.

In particular, preferred compounds are the compounds of formula (I) described in the examples as individual compounds in the form of the free acids, their esters as well as hydrates or solvates and pharmaceutically acceptable salts thereof.

Preferred compounds of formula (I) are those selected from the group consisting of (RS)- and (SR)-(4-carbamimidoyl-phenylamino)-[5-ethoxy-2-fluoro-3-[(RS)-1-methyl-piperidin-3-ylmethoxy]-phenyl]-acetic acid ethyl ester hydrochloride, (RS)- and (SR)-(4-carbamimidoyl-phenylamino)-[5-ethoxy-2-fluoro-3-[(RS)-1-methyl-piperidin-3-ylmethoxy]-phenyl]-acetic acid, (RS)- and (SR)-(4-carbamimidoyl-phenylamino)-[5-ethoxy-2-fluoro-3-[(RS)-1-methyl-piperidin-3-yloxy]-phenyl]-acetic acid ethyl ester hydrochloride, (RS)- and (SR)-(4-carbamimidoyl-phenylamino)-[5-ethoxy-2-fluoro-3-[(RS)-1-methyl-piperidin-3-yloxy]-phenyl]-acetic acid, (RS)-(4-carbamimidoyl-phenylamino)-[5-ethoxy-2-fluoro-3-(2-piperidin-1-yl-ethoxy)-phenyl]-acetic acid ethyl ester hydrochloride, (RS)-(4-carbamimidoyl-phenylamino)-[5-ethoxy-2-fluoro-3-(2-piperidin-1-yl-ethoxy)-phenyl]-acetic acid, (RS)-(4-carbamimidoyl-phenylamino)-[5-ethoxy-2-fluoro-3-(2-piperidin-4-yl-ethoxy)-phenyl]-acetic acid ethyl ester hydrochloride, (RS)-(4-carbamimidoyl-phenylamino)-[5-ethoxy-2-fluoro-3-(2-piperidin-4-yl-ethoxy)-phenyl]-acetic acid, (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid ethyl ester hydrochloride, (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid, (RS)-(4-carbamimidoyl-phenylamino)-[5-ethoxy-2-fluoro-3-(1-methyl-piperidin-4-ylmethoxy)-phenyl]-acetic acid ethyl ester acetate, (RS)-(4-Carbamimidoyl-phenylamino)-[5-ethoxy-2-fluoro-3-(1-methyl-piperidin-4-ylmethoxy)-phenyl]-acetic acid, (RS)-(4-carbamimidoyl-phenylamino)-[5-ethoxy-2-fluoro-3-(piperidin-4-ylmethoxy)-phenyl]-acetic acid ethyl ester acetate, (RS)-(4-carbamimidoyl-phenylamino)-[5-ethoxy-2-fluoro-3-(piperidin-4-ylmethoxy)-phenyl]-acetic acid, (RS)-(4-carbamimidoyl-phenylamino)-[5-ethoxy-3-(1-ethoxycarbonylmethyl-piperidin-4-yloxy)-2-fluoro-phenyl]-acetic acid ethyl ester hydrochloride, (RS)-(4-carbamimidoyl-phenylamino)-[3-(1-carboxymethyl-piperidin-4-yloxy)-5-ethoxy-2-fluoro-phenyl]-acetic acid, (RS)-(4-carbamimidoyl-phenylamino)-{5-ethoxy-2-fluoro-3-[1-(2-hydroxy-ethyl)-piperidin-4-yloxy]-phenyl}-acetic acid ethyl ester hydrochloride, (RS)-(4-carbamimidoyl-phenylamino)-{5-ethoxy-2-fluoro-3-[1-(2-hydroxy-ethyl)-piperidin-4-yloxy]-phenyl}-acetic acid, (RS)- and (SR)-(4-carbamimidoyl-phenylamino)-[5-ethoxy-3-[(RS)-1-ethoxycarbonylmethyl-piperidin-3-yloxy]-2-fluoro-phenyl]-acetic acid ethyl ester hydrochloride, (RS)- and (SR)-(4-carbamimidoyl-phenylamino)-[3-[(RS)-1-carboxymethyl-piperidin-3-yloxy]-5-ethoxy-2-fluoro-phenyl]-acetic acid, (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid ethyl ester hydrochloride, (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid, (RS)-(4-carbamimidoyl-phenylamino)-[5-ethoxy-2-fluoro-3-(piperidin-4-yloxy)-phenyl]-acetic acid ethyl ester hydrochloride, (RS)-(4-carbamimidoyl-phenylamino)-[5-ethoxy-2-fluoro-3-(piperidin-4-yloxy)-phenyl]-acetic acid, (RS)-(4-carbamimidoyl-phenylamino)-[5-ethoxy-2-fluoro-3-(1-methyl-piperidin-4-yloxy)-phenyl]-acetic acid ethyl ester hydrochloride(1:2), (RS)-(4-carbamimidoyl-phenylamino)-[5-ethoxy-2-fluoro-3-(1-methyl-piperidin-4-yloxy)-phenyl]-acetic acid, (S)-(4-carbamimidoyl-phenylamino)-[5-ethoxy-2-fluoro-3-(1-methyl-piperidin-4-yloxy)-phenyl]-acetic acid, and (R)-(4-carbamimidoyl-phenylamino)-[5-ethoxy-2-fluoro-3-(1-methyl-piperidin-4-yloxy)-phenyl]-acetic acid, and pharmaceutically acceptable salts thereof.

Particularly preferred compounds of formula (I) are those selected from the group consisting of
- (RS)- and (SR)-(4-carbamimidoyl-phenylamino)-[5-ethoxy-2-fluoro-3-[(RS)-1-methyl-piperidin-3-yloxy]-phenyl]-acetic acid,
- (RS)-(4-carbamimidoyl-phenylamino)-{5-ethoxy-2-fluoro-3-[1-(2-hydroxy-ethyl)-piperidin-4-yloxy]-phenyl}-acetic acid,
- (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid,
- (RS)-(4-carbamimidoyl-phenylamino)-[5-ethoxy-2-fluoro-3-(piperidin-4-yloxy)-phenyl]-acetic acid,
- (RS)-(4-carbamimidoyl-phenylamino)-[5-ethoxy-2-fluoro-3-(1-methyl-piperidin-4-yloxy)-phenyl]-acetic acid, a (R)-(4-carbamimidoyl-phenylamino)-[5-ethoxy-2-fluoro-3-(1-methyl-piperidin-4-yloxy)-phenyl]-acetic acid, and pharmaceutically acceptable salts thereof It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises converting the nitrile group in a compound of formula (II)

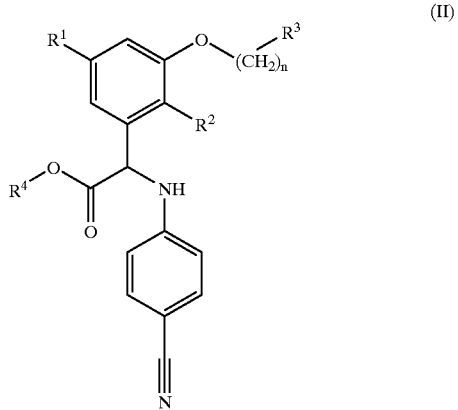

(II)

wherein $R^1$, $R^2$, $R^3$, $R^4$ and n have the significances given above, into a carbamimidoyl group and, if desired, converting an obtained compound of formula (I) into a pharmaceutically acceptable salt or converting a salt of a compound of formula (I) into the corresponding compound of formula (I). A preferred process as described above comprises the conversion of the nitrile group into a carbamamidoyl group and, if desired, converting an obtained compound of formula (I) into a pharmaceutically acceptable salt, more preferably the conversion of the nitrile group into a carbamamidoyl group.

The conversion of the nitrile group in a compound of formula (II) into a carbamimidoyl-group —C(NH)NH$_2$ can be carried out according to methods known per se.

The conversion of the nitrile group into a carbamimidoyl group can be carried out e.g. by treating a compound of formula (II) in a solvent, such as ethanol or methanol, or a solvent mixture, such as chloroform and methanol or chloroform and ethanol, with a dry stream of hydrogen chloride, conveniently at a temperature below 10° C., thereafter treating the reaction solution with a solvent, such as diethyl ether, and filtering off the precipitated iminoether. The thus-obtained material is treated in a solvent, such as methanol or ethanol, either with gaseous ammonia or an ammonium salt, such as ammonium acetate, conveniently at a temperature up to 80° C. Alternatively, the solution containing the iminoether can be evaporated and the residue can be treated with gaseous ammonia or an ammonium salt in methanol or ethanol.

The conversion of the nitrile group in a compound of formula (II) into a carbam-imidoyl group can also be achieved by conversion of the nitrile group into a N-hydroxy-carbamimidoyl group and subsequent reduction. For example, the conversion into a N-hydroxy-carbamimidoyl group can be performed by dissolving a compound of formula (II) in a solvent, such as DMF, ethanol or methanol, treating the solution with hydroxyl-amine or a salt of hydroxylamine with an inorganic acid, such as hydroxylamine hydrochloride, and thereafter with a base, such as diisopropylethylamine or triethylamine, sodium hydride or sodium methanolate, conveniently at a temperature up to 80° C. For the conversion of a N-hydroxy-carbamimidoyl group into a carbamimidoyl group, the compound can be hydrogenated in a solvent, such as ethanol, methanol, dioxan, THF or glacial acetic acid, or a solvent mixture, such as ethanol and glacial acetic acid, with hydrogen and a catalyst, such as palladium, platinum or nickel. In so doing, other reactive groups present in the compound of formula I and reactive towards the reducing agent can be modified.

An ester group ($R^4$=lower-alkyl) can be converted to the carboxy group by methods known in the art, e.g. by hydrolysis with sodium hydroxide in water or water/THF at a temperature in the range of 0 to 30° C. during 1 to 5 hours.

The compounds of formula (II) can be prepared according to general methods known per se, e.g. as described hereinafter and/or as described in the Examples or in analogy to these methods. For example, a compound of formula (III)

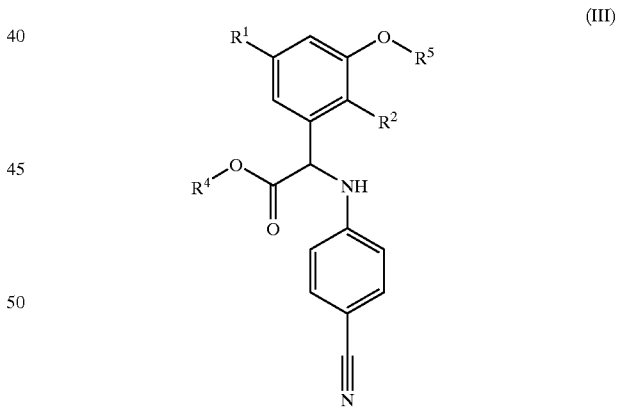

(III)

in which $R^1$, $R^2$ and $R^4$ have the significances given above and $R^5$=H can be reacted: with an alkylating agent such as an appropriately substituted alkyl bromide, alkyl iodide or alkyl mesylate in the presence of a base such as potassium carbonate or caesium carbonate in a solvent such as DMF or acetone, or by a Mitsunobu reaction with an appropriately substituted alkohol in the presence of DEAD, DIAD, or di-tert.-butyl-azodicarboxylate, and triphenylphosphine in a solvent such as THF or dioxane, there are obtained compounds of formula (II)

Suitable piperidinyl-substituted alkyl halogenides or alcohols, which are starting materials for such a reaction, are either commercially available or can be prepared by methods known in the art or in analogy to the examples described.

A compound of formula (III) in which $R^5$ represents hydrogen can be obtained from a compound of formula (III) in which $R^5$ represents a protecting group (e.g. a benzyl group, an isopropyl group or a tert-butyl dimethylsilyl group) by methods known per se, see T. W. Greene, P.G.M Wuts "Protective Groups in Organic Synthesis", $2^{nd}$ ed., John Wiley & Sons, Inc., New York/Chichester/Brisbane/Toronto/Singapore 1991.

The compounds of formula (III) can be prepared according to general methods known per se, e.g. as described hereinafter and/or as described in the Examples or in analogy to these methods. For example, an aldehyde of formula (IV)

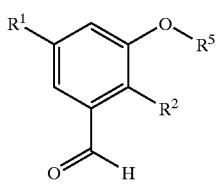
(IV)

in which $R^1$ and $R^2$ have the significances given above and $R^5$ represents hydrogen or a protecting group (e.g. a benzyl group, an isopropyl group or a tert-butyl dimethylsilyl group) can be reacted with a p-aminobenzonitrile of formula (V)

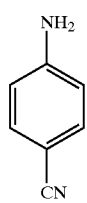
(V)

and benzylisonitrile, toluenesulfonylmethylisonitrile, or morpholinoethylisocyanide, and a primary alkanol such as methanol or ethanol, in the presence of boron trifluoride etherate. Hydrolysis of the resulting iminoether with water yields a compound of formula (III) in which $R^4$ represents methyl or ethyl and $R^5$ represents hydrogen or a protecting group (e.g. a benzyl group, an isopropyl group or a tert-butyl dimethylsilyl group). By hydrolysis of the ester group $R^4$, e.g. by treatment with LiOH in tetrahydrofuran, there is obtained a compound of formula (III) in which $R^4$ represents hydrogen.

Compounds of formula (IV) are known per se or can be prepared according to methods known per se, e.g. as described hereinafter and/or as described in the Examples or in analogy to these methods.

Starting materials for the preparation of compounds of formula (IV) are either commercially available or can be prepared by methods known in the art.

Insofar as their preparation is not described in the examples, the compounds of formulae (I), (II), (III) and (IV) can be prepared according to analogous methods or according to the methods set forth above.

Furthermore, the invention relates to compounds of formula (I) as defined above, when manufactured by a process as described above. In another embodiment, the invention relates to the intermediates, the compounds of formula (II)

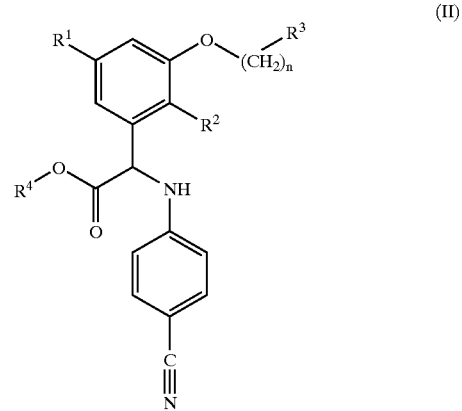
(II)

wherein $R^1$, $R^2$, $R^3$, $R^4$ and n have the significances given above.

As described above, the compounds of formula (I) are active compounds and inhibit the formation of coagulation factors Xa, IXa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumor cells and prevent metastases. They can therefore also be used as antitumor agents. Prevention and/or treatment of thrombosis is the preferred indication.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are associated with the formation of clotting factors Xa, IXa and thrombin induced by factor VIIa and tissue factor, particularly as therapeutically active substances for the treatment and/or prophylaxis of arterial and venous thrombosis, deep vein thrombosis, pulmonary embolism, unstable angina pectoris, cardiac infarction, stroke due to atrial fibrillation, inflammation, arteriosclerosis and/or tumor.

In another preferred embodiment, the invention relates to a method for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor, which method comprises administering a compound as defined above to a human being or animal.

The invention also embraces the use of compounds as defined above for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor.

The invention also relates to the use of compounds as described above for the preparation of medicaments for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor. Such medicaments comprise a compound as described above.

The inhibition of the amidolytic activity of factor VIIa/tissue factor complex by the compounds in accordance with the invention can be demonstrated with the aid of a chromogenic peptide substrate as described hereinafter.

The measurements were carried out on microtiter plates at room temperature. To this end, 100 $\mu$l of a solution of 26 nM of tissue factor, 9 nM of soluble factor VIIa and 8 mM of calcium chloride were added to 25 $\mu$l of a solution of the inhibitor in a buffer [pH 7.5, 100 mM, comprising 0.14M NaCl, 0.1M N-(2-hydroxyethyl)piperadine-N'-(2-ethanesulphonic acid) (HEPES), 0.5 mg/l of fatty-acid-free BSA (bovine serum albumin) and 0.05% $NaN_3$] in each well of the plate. After an incubation time of 15 minutes the reaction was started by the addition of 50 $\mu$l of chromogenic substrate Chromozym-tPA (3.5 mM, $MeSO_2$-D-Phe-Gly-Arg-paranitroanilide) and the hydrolysis of the substrate was followed spectrophotometrically on a kinetic microtiter plate reader over 10 minutes. Using the plot of the inhibition curves, the Ki values were determined according to the method described in Biochem. J. 55, 1953, 170–171.

The activity of the low molecular weight substances can, moreover, be characterized in the "prothrombi" time" (PT) clotting test. The substances are prepared as a 10 mM solution in DMSO or DMSO/0.1M HCl (DHCl) and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 $\mu$l of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 $\mu$l of plasma/inhibitor mixture in the measurement container. The clotting reaction was initiated by the addition of 0.1 ml of Innovin® (recombinant human tissue factor combined with calcium buffer and synthetic phospholipids(Dade Behring®, Inc.). The time up to the fibrin cross-linking was determined photooptically from the ACL. The inhibitor concentration, which brought about a doubling of the PT clotting time, was determined by means of a graph.

The Ki value of the active compounds of the present invention preferably amounts to about 0.1 to 500 nM, especially about 0.1 to 150 nM. The PT values preferably amount to about 0.1 to 10 $\mu$M, especially about 0.1 to 5 $\mu$M.

| Example | PT [$\mu$M] | Solubility (phosphate buffer, pH 6.5) [mg/ml] |
|---|---|---|
| 2.3 | 2.1 | 2.2 |
| 13.3 | 3.6 | 3.3 (pH 5) |
| 13.8 | 1.6 | 5.7 |
| Example 253.a of WO 00/35858 | 4.5 | — |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Parenteral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

13

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

DMA=N,N-dimethylacetamide, EtOAc=ethylacetate, EtOH=ethanol, r.t.=room temperature, DMF=N,N-Dimethylformamide, hrs.=hours, MeOH=methanol.

Example 1

1.1

A solution of 56.3 g 4-ethoxy-fluorophenol in 200 ml THF was treated with 84.0 ml pentamethyl-diethylentriamine, cooled to −78° C., then slowly treated with 251 ml 1.6 M n-butyllithium solution in hexane. The reaction mixture was stirred at −78° C. for 3 hrs and then slowly treated with 89.7 ml trimethyl borate. After stirring for 15 min at −78° C., the solution was warmed up to r.t., stirred for an additional 2 hrs and cooled to 0° C. To the mixture were then added dropwise 63.2 ml acetic acid. After stirring for 30 min, 68.3 ml 30% aqueous hydrogen peroxide solution were added slowly. The reaction mixture was warmed up to r.t., stirred overnight and subsequently treated with 200 ml saturated sodium sulfite solution. The mixture was diluted with water and extracted with hexanes. The organic layer was washed with water and brine, dried over $MgSO_4$, filtrated and concentrated to give 60.3 g 5-ethoxy-2-fluoro-phenol as a light brown liquid which was used for the next step without further purification.

1.2

To a solution of 75.5 g 5-ethoxy-2-fluoro-phenol described in example 1.1 in 250 ml DMA were added 80.2 g t-butyl dimethylchlorsilane and 36.2 g imidazole at 0° C. The reaction mixture was warmed to r.t. After 4 hrs, 400 ml water were added. The mixture was extracted with hexane. The organic layer was washed with water, 10% $Na_2CO_3$ solution, water and brine, dried over $MgSO_4$, filtrated and concentrated to give 127.0 g tert-butyl-(5-ethoxy-2-fluoro-phenoxy)-dimethyl-silane as light brown liquid which was used in the next step without further purification.

1.3

A solution of tert-butyl-(5-ethoxy-2-fluoro-phenoxy)-dimethyl-silane described in example 1.2 in 160 ml THF was treated with 66.9 ml pentamethyl diethylentriamine and cooled to −78° C. 200 ml of 1.6 M n-butyllithium solution in hexanes were added dropwise. The light brown, viscous suspension was stirred at −50° C. to −60° C. for 5 hrs, then treated with 24.7 ml DMF within 20 min. The clear yellow solution was warmed up to r.t. overnight. The reaction was quenched with ice and extracted with EtOAc. The organic layer was dried over $MgSO_4$, filtrated and evaporated to give 51.4 g 3-(tert-butyl-dimethyl-silanyloxy)-5-ethoxy-2-fluoro-benzaldehyde as a brown liquid which was used for the next step without further purification.

1.4

A solution of 16.9 g 3-(tert-butyl-dimethyl-silanyloxy)-5-ethoxy-2-fluoro- obtained from example 1.3 and 6.68 g 4-aminobenzonitrile in 300 ml EtOH was treated with 7.79 ml 2-morpholinoethyl isocyanide and cooled to 0° C. The reaction mixture was treated dropwise with 28.4 ml borontrifluoride etherate such that the temperature did not exceed 10° C. The solution was stirred at 0° C. for 15 min and at r.t. for 3 hrs, then treated with 20 ml of water and warmed to 50° C. overnight. The reaction mixture was evaporated. The residue was taken up in water and extracted with EtOAc.

14

The organic layer was dried over $MgSO_4$. The crude product was purified by chromatography on silica with cyclohexane/EtOAc 2:1 to give 12.9 g (RS)-(4-cyano-phenylamino)-(5-ethoxy-2-fluoro-3-hydroxy-phenyl)-acetic acid ethyl ester as a light brown foam. MS: 357.1 ([M−H]⁻).

1.5

A solution of 269 mg g (RS)-(4-cyano-phenylamino)-(5-ethoxy-2-fluoro-3-hydroxy-phenyl)-acetic acid ethyl ester in 10 ml THF was treated with 0.115 ml 1-methyl-3-piperidine-methanol and 236 mg triphenylphosphin. The reaction mixture was cooled to 0° C., and 207 mg di-tert-butyl azodicarboxylate were added. After stirring for 6 hrs at r.t., the solution was concentrated. The product was isolated by chromatography on silica with dichloromethane/methanol 9:1 to give 212 mg (RS)- and (SR)-(4-cyano-phenylamino)-[5-ethoxy-2-fluoro-3-[(RS)-1-methyl-piperidin-3-ylmethoxy]-phenyl]-acetic acid ethyl ester as a white solid. MS: 470.3 ([M+H]⁺).

1.6

Through a solution of 212 mg (RS)- and (SR)-(4-cyano-phenylamino)-[5-ethoxy-2-fluoro-3-[(RS)-1-methyl-piperidin-3-ylmethoxy]-phenyl]-acetic acid ethyl ester in 5 ml CHCl3/EtOH 3:1 was passed a stream of HCl at −10° C. during 20 min. The reaction mixture was stored at 4° C. overnight, then concentrated, dried in the HV, treated with 2 ml 2M $NH_3$-solution in EtOH and heated to 60° C. for 3 hrs. The suspension was concentrated. The crude product was isolated by chromatography on silica using dichloromethane/MeOH 4:1 to yield 229 mg (RS)- and (SR)-(4-carbamimidoyl-phenylamino)-[5-ethoxy-2-fluoro-3-[(RS)-1-methyl-piperidin-3-ylmethoxy]-phenyl]-acetic acid ethyl ester hydrochloride as an off-white solid. MS: 487.3 ([M+H]⁺).

1.7

To a solution of 174 mg (RS)- and (SR)-(4-carbamimidoyl-phenylamino)-[5-ethoxy-2-fluoro-3-[(RS)-1-methyl-piperidin-3-ylmethoxy]-phenyl]-acetic acid ethyl ester hydrochloride in 3.5 ml THF were added 1.7 ml 1N LiOH solution at 0° C. The reaction mixture was stirred for 2 hrs at r.t., then neutralized with 1N HCl solution. The precipitate was filtered off and washed with water, acetonitrile and pentane to give 97 mg (RS)- and (SR)-(4-carbamimidoyl-phenylamino)-[5-ethoxy-2-fluoro-3-[(RS)-1-methyl-piperidin-3-ylmethoxy]-phenyl]-acetic acid as a light yellow solid. MS: 459.3 ([M+H]⁺).

Example 2

2.1

In analogy to example 1.5, (RS)-(4-cyano-phenylamino)-(5-ethoxy-2-fluoro-3-hydroxy-phenyl)-acetic acid ethyl ester described in example 1.4 was reacted with 3-hydroxy-1-methyl-piperidine to give (RS)- and (SR)-(4-cyano-phenylamino)-[5-ethoxy-2-fluoro-3-[(RS)-1-methyl-piperidin-3-yloxy]-phenyl]-acetic acid ethyl ester. MS: 456.5 ([M+H]⁺).

2.2

In analogy to example 1.6, (RS)- and (SR)-(4-cyano-phenylamino)-[5-ethoxy-2-fluoro-3-[(RS)-1-methyl-piperidin-3-yloxy]-phenyl]-acetic acid ethyl ester was converted to (RS)- and (SR)-(4-carbamimidoyl-phenylamino)-[5-ethoxy-2-fluoro-3-[(RS)-1-methyl-piperidin-3-yloxy]-phenyl]-acetic acid ethyl ester hydrochloride. MS: 473.3 ([M+H]⁺).

2.3

In analogy to example 1.7, (RS)- and (SR)-(4-carbamimidoyl-phenylamino)-[5-ethoxy-2-fluoro-3-[(RS)-1-methyl-piperidin-3-yloxy]-phenyl]-acetic acid ethyl ester hydrochloride was converted to (RS)- and (SR)-(4- carbamimidoyl-phenylamino)-[5-ethoxy-2-fluoro-3-[(RS)-1-methyl-piperidin-3-yloxy]-phenyl]-acetic acid. MS: 445.4 ([M+H]$^+$).

Example 3

3.1

In analogy to example 1.5, (RS)-(4-cyano-phenylamino)-(5-ethoxy-2-fluoro-3-hydroxy-phenyl)-acetic acid ethyl ester described in example 1.4 was first reacted with 1-(2-hydroxyethyl)-piperidine, diethyl azodicarboxylate and triphenylphosphine. Subsequent conversion in analogy to example 1.6 gave (RS)-(4-carbamimidoyl-phenylamino)-[5-ethoxy-2-fluoro-3-(2-piperidin-1-yl-ethoxy)-phenyl]-acetic acid ethyl ester hydrochloride as an off-white, amorphous solid. MS: 487.3 ([M+H]$^+$).

3.2

In analogy to example 1.7, (RS)-(4-carbamimidoyl-phenylamino)-[5-ethoxy-2-fluoro-3-(2-piperidin-1-yl-ethoxy)-phenyl]-acetic acid ethyl ester hydrochloride described in example 3.1 was converted to (RS)-(4-carbamimidoyl-phenylamino)-[5-ethoxy-2-fluoro-3-(2-piperidin-1-yl-ethoxy)-phenyl]-acetic acid. Colorless solid. MS: 459.5 ([M+H]$^+$).

Example 4

4.1

In analogy to example 1.5, (RS)-(4-cyano-phenylamino)-(5-ethoxy-2-fluoro-3-hydroxy-phenyl)-acetic acid ethyl ester described in example 1.4 was reacted with 4-(2-hydroxy-ethyl)-piperidine-1-carboxylic acid tert-butyl ester, diethyl azodicarboxylate and triphenylphosphine to give (RS)-4-(2-{3-[(4-cyano-phenylamino)-ethoxycarbonyl-methyl]-5-ethoxy-2-fluoro-phenoxy}-ethyl)-piperidine-1-carboxylic acid tert-butyl ester as a colorless solid. MS: 570.2 ([M+H]$^+$).

4.2

In analogy to example 1.6, (RS)-4-(2-{3-[(4-cyano-phenylamino)-ethoxycarbonyl-methyl]-5-ethoxy-2-fluoro-phenoxy}-ethyl)-piperidine-1-carboxylic acid tert-butyl ester described in example 4.1 was converted to (RS)-(4-carbamimidoyl-phenylamino)-[5-ethoxy-2-fluoro-3-(2-piperidin-4-yl-ethoxy)-phenyl]-acetic acid ethyl ester hydrochloride. Colorless, amorphous solid. MS: 486.3 ([M+H]$^+$).

4.3

In analogy to example 1.7, (RS)-(4-carbamimidoyl-phenylamino)-[5-ethoxy-2-fluoro-3-(2-piperidin-4-yl-ethoxy)-phenyl]-acetic acid ethyl ester hydrochloride described in example 4.2 was converted to (RS)-(4-carbamimidoyl-phenylamino)-[5-ethoxy-2-fluoro-3-(2-piperidin-4-yl-ethoxy)-phenyl]-acetic acid. Off-white solid. MS: 459.6 ([M+H]$^+$).

Example 5

5.1

In analogy to example 1.5, (RS)-(4-cyano-phenylamino)-(5-ethoxy-2-fluoro-3-hydroxy-phenyl)-acetic acid ethyl ester described in example 1.4 was reacted with α-methyl-1-piperidineethanol to give (RS)- and (SR)-(4-cyano-phenylamino)-[5-ethoxy-2-fluoro-3-[(RS)-1-methyl-2-piperidin-1-yl-ethoxy]-phenyl]-acetic acid ethyl ester. MS: 484.5 ([M+H]$^+$).

5.2

In analogy to example 1.6, (RS)- and (SR)-(4-cyano-phenylamino)-[5-ethoxy-2-fluoro-3-[(RS)-1-methyl-2-piperidin-1-yl-ethoxy]-phenyl]-acetic acid ethyl ester was converted to (RS)- and (SR)-(4-carbamimidoyl-phenylamino)-[5-ethoxy-2-fluoro-3-[(RS)-1-methyl-2-piperidin-1-yl-ethoxy]-phenyl ]-acetic acid ethyl ester hydrochloride. MS: 501.4 ([M+H]$^+$).

5.3

In analogy to example 1.7, (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid ethyl ester hydrochloride was converted to (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid. MS: 473.4 ([M+H]$^+$).

Example 6

6.1

In analogy to example 1.5, (RS)-(4-cyano-phenylamino)-(5-ethoxy-2-fluoro-3-hydroxy-phenyl)-acetic acid ethyl ester, (1-methyl-piperidin-4-yl)-methanol, triphenylphosphine and diethyl azodicarboxylate were converted to (RS)-(4-cyano-phenylamino)-[5-ethoxy-2-fluoro-3-(1-methyl-piperidin-4-ylmethoxy)-phenyl]-acetic acid ethyl ester. Light brown solid. MS: 470 ([M+H]$^+$).

6.2

Hydrogen chloride gas was bubbled into a solution of 362 mg (RS)-(4-cyano-phenylamino)-[5-ethoxy-2-fluoro-3-(1-methyl-piperidin-4-ylmethoxy)-phenyl]-acetic acid ethyl ester in 15 ml methylene chloride and 3 ml ethanol at 0° C. for 30 minutes. The mixture was allowed to slowly come to room temperature over night. The solvents were evaporated in vacuo and the residue shortly dried. 238 mg ammonium acetate and 8 ml ethanol were added and the mixture heated to 65° C. for 4 hours. The solvent was evaporated in vacuo and the residue purified on a short column of silica gel. 348 mg (RS)-(4-carbamimidoyl-phenylamino)-[5-ethoxy-2-fluoro-3-(1-methyl-piperidin-4-ylmethoxy)-phenyl]-acetic acid ethyl ester acetate, were obtained. Light brown solid. MS: 487 ([M+H]$^+$).

6.3

A solution of 340 mg (RS)-(4-carbamimidoyl-phenylamino)-[5-ethoxy-2-fluoro-3-(1-methyl-piperidin-4-ylmethoxy)-phenyl]-acetic acid ethyl ester acetate in 5 ml THF was treated with 2.8 ml 1N LiOH and stirred at room temperature for 2 hours. The reaction mixture was neutralized with acetic acid and evaporated in vacuo. The residue was stirred in 1.5 ml of water. Suction filtration and drying gave 173 mg (RS)-(4-carbamimidoyl-phenylamino)-[5-ethoxy-2-fluoro-3-(1-methyl-piperidin-4-ylmethoxy)-phenyl]-acetic acid. Mp.: 232° C. Light brown solid. MS: 459 ([M+H]$^+$).

Example 7

7.1

In analogy to example 1.5, (RS)-(4-cyano-phenylamino)-(5-ethoxy-2-fluoro-3-hydroxy-phenyl)-acetic acid ethyl ester, 4-hydroxymethyl-piperidine-1-carboxylic acid tert-butyl ester, triphenylphosphine and diethyl azodicarboxylate were converted to (RS)-4-{3-[(4-cyano-phenylamino)-ethoxycarbonyl-methyl]-5-ethoxy-2-fluoro-phenoxymethyl}-piperidine-1-carboxylic acid tert-butyl ester. Light yellow foam. MS: 556 ([M+H]$^+$).

7.2

In analogy to example 6.2, (RS)-4-{3-[(4-cyano-phenylamino)-ethoxycarbonyl-methyl]-5-ethoxy-2-fluoro-phenoxymethyl}-piperidine-1-carboxylic acid tert-butyl ester was converted to (RS)-(4-carbamimidoyl-phenylamino)-[5-ethoxy-2-fluoro-3-(piperidin-4-ylmethoxy)-phenyl]-acetic acid ethyl ester acetate. Off-white solid. MS: 473 ([M+H]$^+$).

7.3

In analogy to example 6.3, (RS)-(4-carbamimidoyl-phenylamino)-[5-ethoxy-2-fluoro-3-(piperidin-4- ylmethoxy)-phenyl]-acetic acid ethyl ester acetate was converted to (RS)-(4-carbamimidoyl-phenylamino)-[5-ethoxy-2-fluoro-3-(piperidin-4-ylmethoxy)-phenyl]-acetic acid. White solid. Mp.: 262° C., MS: 445 ([M+H]$^+$).

8.1

In analogy to example 1.5, (RS)-(4-cyano-phenylamino)-(5-ethoxy-2-fluoro-3-hydroxy-phenyl)-acetic acid ethyl ester described in example 1.4 was reacted with 1-tert-butyloxycarbonyl-4-hydroxy-piperidine to give (RS)-4-{3-[(4-cyano-phenylamino)-ethoxycarbonyl-methyl]-5-ethoxy-2-fluoro-phenoxy}-piperidine-1-carboxylic acid tert-butyl ester. MS: 559.5 ([M+H]$^+$).

8.2

A solution of 2.30 g (RS)-4-{3-[(4-cyano-phenylamino)-ethoxycarbonyl-methyl]-5-ethoxy-2-fluoro-phenoxy}-piperidine-1-carboxylic acid tert-butyl ester in 40 ml dichloromethane was cooled to 0° C. and treated dropwise with 3.25 ml trifluoroacetic acid. The reaction mixture was warmed to r.t. within 3 hrs, then again cooled to 0° C. and treated with 20 ml of 10% Na$_2$CO$_3$ solution. The product was extracted with dichloromethane. The organic layer was dried over MgSO$_4$, filtrated and evaporated to give 1.55 g (RS)-(4-cyano-phenylamino)-[5-ethoxy-2-fluoro-3-(piperidin-4-yloxy)-phenyl]-acetic acid ethyl ester as an off-white solid foam which was used for the next step without further purification. MS: 442.3 ([M+H]$^+$).

8.3

A solution of 300 mg (RS)-(4-cyano-phenylamino)-[5-ethoxy-2-fluoro-3-(piperidin-4-yloxy)-phenyl]-acetic acid ethyl ester in 10 ml THF was cooled to 0° C. and treated with 0.14 ml triethylamine and 0.90 ml bromoacetic acid ethyl ester. The reaction mixture was stirred at r.t. overnight, then evaporated. The residue was taken up in water and extracted with EtOAc. The organic layer was dried over MgSO$_4$. The crude product was purified by chromatography on silica with cyclohexane/EtOAc 1:2 to give 215 mg (RS)-(4-cyano-phenylamino)-[5-ethoxy-3-(1-ethoxycarbonylmethyl-piperidin-4-yloxy)-2-fluoro-phenyl]-acetic acid ethyl ester as a colorless foam. MS: 528.3 ([M+H]$^+$).

8.4

In analogy to example 1.6, (RS)-(4-cyano-phenylamino)-[5-ethoxy-3-(1-ethoxycarbonylmethyl-piperidin-4-yloxy)-2-fluoro-phenyl]-acetic acid ethyl ester was converted to (RS)-(4-carbamimidoyl-phenylamino)-[5-ethoxy-3-(1-ethoxycarbonylmethyl-piperidin-4-yloxy)-2-fluoro-phenyl]-acetic acid ethyl ester hydrochloride. MS: 545.2 ([M+H]$^+$).

8.5

In analogy to example 1.7, (RS)-(4-carbamimidoyl-phenylamino)-[5-ethoxy-3-(1-ethoxycarbonylmethyl-piperidin-4-yloxy)-2-fluoro-phenyl]-acetic acid ethyl ester hydrochloride was converted to (RS)-(4-carbamimidoyl-phenylamino)-[3-(1-carboxymethyl-piperidin-4-yloxy)-5-ethoxy-2-fluoro-phenyl]-acetic acid. MS: 489.3 ([M+H]$^+$).

Example 9

9.1

A solution of 300 mg (RS)-(4-cyano-phenylamino)-[5-ethoxy-2-fluoro-3-(piperidin-4-yloxy)-phenyl]-acetic acid ethyl ester described in example 11.2 in 10 ml THF was treated with 0.19 ml triethylamine, 0.82 ml 2-bromoethanol and 25 mg tetrabutylammonium iodide. The reaction mixture was heated to 50° C. for 6 hrs, then evaporated. The residue was taken up in water and extracted with EtOAc. The crude product was purified by chromatography on silica with dichloromethane/MeOH 9:1 to give 175 mg (RS)-(4-cyano-phenylamino)-{5-ethoxy-2-fluoro-3-[1-(2-hydroxy-ethyl)-piperidin-4-yloxy]-phenyl}acetic acid ethyl ester. MS: 486.4 ([M+H]$^+$).

9.2

In analogy to example 1.6, (RS)-(4-cyano-phenylamino)-{5-ethoxy-2-fluoro-3-[1-(2-hydroxy-ethyl)-piperidin-4-yloxy]-phenyl}-acetic acid ethyl ester was converted to (RS)-(4-carbamimidoyl-phenylamino)-{5-ethoxy-2-fluoro-3-[1-(2-hydroxy-ethyl)-piperidin-4-yloxy]-phenyl}-acetic acid ethyl ester hydrochloride. MS: 503.4 ([M+H]$^+$).

9.3

In analogy to example 1.7, (RS)-(4-carbamimidoyl-phenylamino)-{5-ethoxy-2-fluoro-3-[1-(2-hydroxy-ethyl)-piperidin-4-yloxy]-phenyl}-acetic acid ethyl ester hydrochloride was converted to (RS)-(4-carbamimidoyl-phenylamino)-{5-ethoxy-2-fluoro-3-[1-(2-hydroxy-ethyl)-piperidin-4-yloxy]-phenyl}-acetic acid. MS: 475.3 ([M+H]$^+$).

Example 10

10.1

In analogy to example 1.5, (RS)-(4-cyano-phenylamino)-(5-ethoxy-2-fluoro-3-hydroxy-phenyl)-acetic acid ethyl ester described in example 1.4 was reacted with (RS)-1-tert-butyloxycarbonyl-3-hydroxy-piperidine to give (SR)- and (RS)-3-[3-[(RS)-(4-cyano-phenylamino)-ethoxycarbonyl-methyl]-5-ethoxy-2-fluoro-phenoxy]-piperidine-1-carboxylic acid tert-butyl ester. MS: 542.2 ([M+H]$^+$).

10.2

In analogy to example 8.2, (SR)- and (RS)-3-[3-[(RS)-(4-cyano-phenylamino)-ethoxycarbonyl-methyl ]-5-ethoxy-2-fluoro-phenoxy]-piperidine-1-carboxylic acid tert-butyl ester was converted to (SR)- and (RS)-(4-Cyano-phenylamino)-[5-ethoxy-2-fluoro-3-[(RS)-piperidin-3-yloxy]-phenyl]-acetic acid ethyl ester. MS: 442.3 ([M+H]$^+$).

10.3

In analogy to example 8.3, (SR)- and (RS)-(4-cyano-phenylamino)-[5-ethoxy-2-fluoro-3-[(RS)-piperidin-3-yloxy]-phenyl]-acetic acid ethyl ester was reacted with bromoacetic acid ethyl ester to give (RS)- and (SR)-(4-cyano-phenylamino)-[5-ethoxy-3-[(RS)-1-ethoxycarbonylmethyl-piperidin-3-yloxy]-2-fluoro-phenyl]-acetic acid ethyl ester. MS: 528.3 ([M+H]$^+$).

10.4

In analogy to example 1.6, (RS)- and (SR)-(4-cyano-phenylamino)-[5-ethoxy-3-[(RS)-1-ethoxycarbonylmethyl-piperidin-3-yloxy]-2-fluoro-phenyl]-acetic acid ethyl ester was converted to (RS)- and (SR)-(4-carbamimidoyl-phenylamino)-[5-ethoxy-3-[(RS)-1-ethoxycarbonylmethyl-piperidin-3-yloxy]-2-fluoro-phenyl]-acetic acid ethyl ester hydrochloride. MS: 545.2 ([M+H]$^+$).

10.5

In analogy to example 1.7, (RS)- and (SR)-(4-carbamimidoyl-phenylamino)-[5-ethoxy-3-[(RS)-1-ethoxycarbonylmethyl-piperidin-3-yloxy]-2-fluoro-phenyl]-acetic acid ethyl ester hydrochloride was converted to (RS)- and (SR)-(4-carbamimidoyl-phenylamino)-[3-[(RS)-1-carboxymethyl-piperidin-3-yloxy]-5-ethoxy-2-fluoro-phenyl]-acetic acid. MS: 489.3 ([M+H]$^+$).

Example 11

11.1

In analogy to example 9.1, (SR)- and (RS)-(4-Cyano-phenylamino)-[5-ethoxy-2-fluoro-3-[(RS)-piperidin-3-yloxy]-phenyl]-acetic acid ethyl ester described in example 10.2 was reacted with 2-bromoethanol to give (RS)- and (SR)-(4-cyano-phenylamino)-{5-ethoxy-2-fluoro-3-[(RS)-1-(2-hydroxy-ethyl)-piperidin-3-yloxy]-phenyl}-acetic acid ethyl ester. MS: 486.4 ([M+H]$^+$).

11.2

In analogy to example 1.6, (RS)- and (SR)-(4-cyano-phenylamino)-{5-ethoxy-2-fluoro-3-[(RS)-1-(2-hydroxyethyl)-piperidin-3-yloxy]-phenyl}-acetic acid ethyl ester was converted to (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid ethyl ester hydrochloride. MS: 503.3 ([M+H]$^+$).

11.3

In analogy to example 1.7, (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid ethyl ester hydrochloride was converted to (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid. MS: 475.3 ([M+H]$^+$).

Example 12

12.1

In analogy to example 1.6, (RS)-(4-cyano-phenylamino)-[5-ethoxy-2-fluoro-3-(piperidin-4-yloxy)-phenyl]-acetic acid ethyl ester described in example 11.2 was converted to (RS)-(4-carbamimidoyl-phenylamino)-[5-ethoxy-2-fluoro-3-(piperidin-4-yloxy)-phenyl]-acetic acid ethyl ester hydrochloride. MS: 459.5 ([M+H]$^+$).

12.2

In analogy to example 1.7, (RS)-(4-carbamimidoyl-phenylamino)-[5-ethoxy-2-fluoro-3-(piperidin-4-yloxy)-phenyl]-acetic acid ethyl ester hydrochloride was converted to (RS)-(4-carbamimidoyl-phenylamino)-[5-ethoxy-2-fluoro-3-(piperidin-4-yloxy)-phenyl]-acetic acid. MS: 431.5 ([M+H]$^+$).

Example 13

13.1

In analogy to example 1.5, (RS)-(4-cyano-phenylamino)-(5-ethoxy-2-fluoro-3-hydroxy-phenyl)-acetic acid ethyl ester and 4-hydroxy-1-methyl-piperidine were converted to (RS)-(4-cyano-phenylamino)-[5-ethoxy-2-fluoro-3-(1-methyl-piperidin-4-yloxy)-phenyl]-acetic acid ethyl ester. Light brown soldi foam. MS: 456 ([M+H]$^+$).

13.2

In analogy to example 6.2, (RS)-(4-cyano-phenylamino)-[5-ethoxy-2-fluoro-3-(1-methyl-piperidin-4-yloxy)-phenyl]-acetic acid ethyl ester was transformed to (RS)-(4-carbamimidoyl-phenylamino)-[5-ethoxy-2-fluoro-3-(1-methyl-piperidin-4-yloxy)-phenyl]-acetic acid ethyl ester, hydrochloride (1:2). Viscous oil. MS: 473 ([M+H]$^+$).

13.3

In analogy to example 6.3, (RS)-(4-carbamimidoyl-phenylamino)-[5-ethoxy-2-fluoro-3-(1-methyl-piperidin-4-yloxy)-phenyl]-acetic acid ethyl ester, hydrochloride was converted to (RS)-(4-carbamimidoyl-phenylamino)-[5-ethoxy-2-fluoro-3-(1-methyl-piperidin-4-yloxy)-phenyl]-acetic acid. Off-white solid. Mp.: 270° C. MS: 445 ([M+H]$^+$).

13.4

A solution of 2.5 g (RS)-(4-carbamimidoyl-phenylamino)-[5-ethoxy-2-fluoro-3-(1-methyl-piperidin-4-yloxy)-phenyl]-acetic acid ethyl ester hydrochloride described in example 13.2 in 50 ml dichloromethane was treated with 1.1 g di-tert-butyl dicarbonate, 25 ml water and 25 ml saturated aqueous sodium carbonate solution. The reaction mixture was stirred at room temperature for 2 hrs. Extraction with ethyl acetate, water and brine, followed by chromatography on silica gel with dichloromethane/methanol gave 2.3 g (RS)-[4-(tert-butoxycarbonylamino-imino-methyl)-phenylamino]-[5-ethoxy-2-fluoro-3-(1-methyl-piperidin-4-yloxy)-phenyl]-acetic acid ethyl ester as a light yellow foam. MS: 573 ([M+H]$^+$).

13.5

A solution of 2.3 g (RS)-[4-(tert-butoxycarbonylamino-imino-methyl)-phenylamino]-[5-ethoxy-2-fluoro-3-(1-methyl-piperidin-4-yloxy)-phenyl]-acetic acid ethyl ester in 23 ml ethanol was treated with 6.06 ml 1N sodium hydroxyde solution. After one hour, 2.6 ml 1N hydrochloric acid were added until pH=8. The solvent was evaporated and the residue dried to constant weight. It was dissolved in absolute ethanol, filtered, the solution evaporated in vacuo, the residue dried and triturated in ether to yield 2.3 g of (RS)-[4-(tert-butoxycarbonylamino-imino-methyl)-phenylamino]-[5-ethoxy-2-fluoro-3-(1-methyl-piperidin-4-yloxy)-phenyl]-acetic acid.off-white solid. MS: 545 ([M+H]$^+$).

13.6

The racemic (RS)-[4-(tert-butoxycarbonylamino-imino-methyl)-phenylamino]-[5-ethoxy-2-fluoro-3-(1-methyl-piperidin-4-yloxy)-phenyl]-acetic acid was separated into the enantiomers by preparative HPLC on a chiral column (Chiralpack AD; n-heptane/ethanol/diethylamine 78:22:0.2) to give the first eluted (S)-[4-(tert-butoxycarbonylamino-imino-methyl)-phenylamino]-[5-ethoxy-2-fluoro-3-(1-methyl-piperidin-4-yloxy)-phenyl]-acetic acid, MS: 545 (M+H)$^+$ and the second e®ed (R)-[4-(tert-butoxycarbonylamino-imino-methyl)-phenylamino]-[5-ethoxy-2-fluoro-3-(1-methyl-piperidin-4-yloxy)-phenyl]-acetic acid. Both light yellow solid foam. MS: 545 ([M+H]$^+$).

13.7

A solution of 5.1 g (S)-[4-(tert-butoxycarbonylamino-imino-methyl)-phenylamino]-[5-ethoxy-2-fluoro-3-(1-methyl-piperidin-4-yloxy)-phenyl]-acetic acid in 102 ml water/formic acid 1:1 was heated to 40° C. for 2.5 hrs. The solvents were evaporated in vacuo, the residue dissolved in water and the solution evaporated again (repeated twice). The residue was dissolved in methanol and 7N methanolic ammonia was added until pH=9, wereby a precipitate was formed. The mixture was cooled to 0° C., the solid isolated by suction filtration and dried. Afterwards it was suspended in water and the pH adjusted to 9 wiTh conc. ammonia. Suction filtration and drying gave 3 g (S)-(4-carbamimidoyl-phenylamino)-[5-ethoxy-2-fluoro-3-(1-methyl-piperidin-4-yloxy)-phenyl]-acetic acid. White solid. Mp.: 269° C. MS: 445 ([M+H]$^+$).

13.8

In analogy to examp® 13.7, (R)-[4-(tert-butoxycarbonylamino-imino-methyl)-phenylamino]-[5-ethoxy-2-fluoro-3-(1-methyl-piperidin-4-yloxy)-phenyl]-acetic acid was c®erted to (R)-(4-carbamimidoyl-phenylamino)-[5-ethoxy-2-fluoro-3-(1-methyl-piperidin-4-yloxy)-phenyl]-acetic acid. White solid. Mp.: 267° C. MS: 445 ([M+H]$^+$).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |

-continued

| Ingredients | Per tablet | |
|---|---|---|
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |

-continued

| | |
|---|---|
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg |
| | (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The subject invention has been described in terms of its preferred embodiments. Upon reading this specification, vaious alternative embodiments will become obvious to skilled in the art. These variations are to be considered within the scope and spirit of the subject invention which is only to be limited by the claims that follow and to their equivalents.

What is claimed is:

1. A compound of the formula:

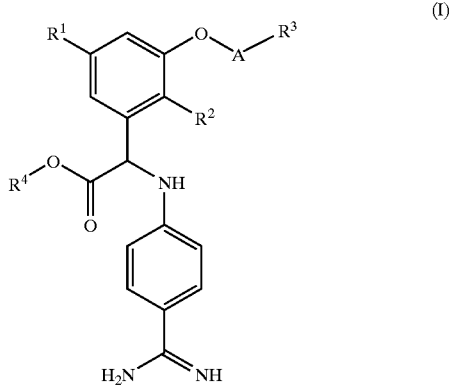

wherein
  $R^1$ is lower-alkoxy;
  $R^2$ is halogen;
  $R^3$ is piperidinyl or piperidinyl substituted with lower-alkyl, hydroxy-lower-alkyl, carboxy-lower-alkyl or lower-alkoxy-carbonyl-lower-alkyl;

R⁴ is hydrogen or lower-alkyl;
A is —(CH$_2$)$_n$— or —(CH$_2$)$_n$— which is substituted with lower-alkyl; and
n is 0 to 3;
or a pharmaceutically acceptable salt thereof.

2. The compound according to claim 1, wherein R¹ is ethoxy.

3. The compound according to claim 1, wherein R² is fluorine.

4. The compound according to claim 1, wherein R³ is piperidinyl or piperidinyl substituted with methyl or hydroxy-ethyl.

5. The compound according to claim 4, wherein R³ is 1-methyl-piperidin-3-yl; 1-(2-hydroxy-ethyl)-piperidin-4-yl; 1-(2-hydroxy-ethyl)-piperidin-3-yl; piperidin-4-yl; or 1-methyl-piperidin-4-yl.

6. The compound according to claim 1, wherein R⁴ is hydrogen or ethyl.

7. The compound according to claim 6, wherein R⁴ is hydrogen.

8. The compounds according to claim 1, wherein n is 0 to 2.

9. The compound according to claim 8, wherein n is 0.

10. The compound according to claim 1 which is (RS)- and (SR)-(4-carbamimidoyl-phenylamino)-[5-ethoxy-2-fluoro-3-[(RS)-1-methyl-piperidin-3-ylmethoxy]-phenyl]-acetic acid ethyl ester hydrochloride or a pharmaceutically acceptable salt thereof.

11. The compound according to claim 1 which is (RS)- and (SR)-(4-carbamimidoyl-phenylamino)-[5-ethoxy-2-fluoro-3-[(RS)-1-methyl-piperidin-3-ylmethoxy]-phenyl]-acetic acid or a pharmaceutically acceptable salt thereof.

12. The compound according to claim 1 which is (RS)- and (SR)-(4-carbamimidoyl-phenylamino)-[5-ethoxy-2-fluoro-3-[(RS)-1-methyl-piperidin-3-yloxy]-phenyl]-acetic acid ethyl ester hydrochloride or a pharmaceutically acceptable salt thereof.

13. The compound according to claim 1 which is (RS)- and (SR)-(4-carbamimidoyl-phenylamino)-[5-ethoxy-2-fluoro-3-[(RS)-1-methyl-piperidin-3-yloxy]-phenyl]-acetic acid or a pharmaceutically acceptable salt thereof.

14. The compound according to claim 1 which is (RS)-(4-carbamimidoyl-phenylamino)-[5-ethoxy-2-fluoro-3-(2-piperidin-1-yl-ethoxy)-phenyl]-acetic acid ethyl ester hydrochloride or a pharmaceutically acceptable salt thereof.

15. The compound according to claim 1 which is (RS)-(4-carbamimidoyl-phenylamino)-[5-ethoxy-2-fluoro-3-(2-piperidin-1-yl-ethoxy)-phenyl]-acetic acid or a pharmaceutically acceptable salt thereof.

16. The compound according to claim 1 which is (RS)-(4-carbamimidoyl-phenylamino)-[5-ethoxy-2-fluoro-3-(2-piperidin-4-yl-ethoxy)-phenyl]-acetic acid ethyl ester hydrochloride or a pharmaceutically acceptable salt thereof.

17. The compound according to claim 1 which is (RS)-(4-carbamimidoyl-phenylamino)-[5-ethoxy-2-fluoro-3-(2-piperidin-4-yl-ethoxy)-phenyl]-acetic acid or a pharmaceutically acceptable salt thereof.

18. The compound according to claim 1 which is (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid ethyl ester hydrochloride or a pharmaceutically acceptable salt thereof.

19. The compound according to claim 1 which is (RS)- and (SR)-(4-carbamimidoyl-phenylamino)-[5-ethoxy-2-fluoro-3-[(RS)-1-methyl-2-piperidin-1-yl-ethoxy]-phenyl]-acetic acid or a pharmaceutically acceptable salt thereof.

20. The compound according to claim 1 which is (RS)-(4-carbamimidoyl-phenylamino)-[5-ethoxy-2-fluoro-3-(1-methyl-piperidin-4-ylmethoxy)-phenyl]-acetic acid ethyl ester acetate or a pharmaceutically acceptable salt thereof.

21. The compound according to claim 1 which is (RS)-(4-Carbamimidoyl-phenylamino)-[5-ethoxy-2-fluoro-3-(1-methyl-piperidin-4-ylmethoxy)-phenyl]-acetic acid or a pharmaceutically acceptable salt thereof.

22. The compound according to claim 1 which is (RS)-(4-carbamimidoyl-phenylamino)-[5-ethoxy-2-fluoro-3-(piperidin-4-ylmethoxy)-phenyl]-acetic acid ethyl ester acetate or a pharmaceutically acceptable salt thereof.

23. The compound according to claim 1 which is (RS)-(4-carbamimidoyl-phenylamino)-[5-ethoxy-2-fluoro-3-(piperidin-4-ylmethoxy)-phenyl]-acetic acid or a pharmaceutically acceptable salt thereof.

24. The compound according to claim 1 which is (RS)-(4-carbamimidoyl-phenylamino)-[5-ethoxy-3-(1-ethoxycarbonylmethyl-piperidin-4-yloxy)-2-fluoro-phenyl]-acetic acid ethyl ester hydrochloride or a pharmaceutically acceptable salt thereof.

25. The compound according to claim 1 which is (RS)-(4-carbamimidoyl-phenylamino)-[3-(1-carboxymethyl-piperidin-4-yloxy)-5-ethoxy-2-fluoro-phenyl]-acetic acid or a pharmaceutically acceptable salt thereof.

26. The compound according to claim 1 which is (RS)-(4-carbamimidoyl-phenylamino)-{5-ethoxy-2-fluoro-3-[1-(2-hydroxy-ethyl)-piperidin-4-yloxy]-phenyl}acid ethyl ester hydrochloride or a pharmaceutically acceptable salt thereof.

27. The compound according to claim 1 which is (RS)-(4-carbamimidoyl-phenylamino)-{5-ethoxy-2-fluoro-3-[1-(2-hydroxy-ethyl)-piperidin-4-yloxy]-phenyl}-acetic acid or a pharmaceutically acceptable salt thereof.

28. The compound according to claim 1 which is (RS)- and (SR)-(4-carbamimidoyl-phenylamino)-[5-ethoxy-3-[(RS)-1-ethoxycarbonylmethyl-piperidin-3-yloxy]-2-fluoro-phenyl]-acetic acid ethyl ester hydrochloride or a pharmaceutically acceptable salt thereof.

29. The compound according to claim 1 which is (RS)- and (SR)-(4-carbamimidoyl-phenylamino)-[3-[(RS)-1-carboxymethyl-piperidin-3-yloxy]-5-ethoxy-2-fluoro-phenyl]-acetic acid or a pharmaceutically acceptable salt thereof.

30. The compound according to claim 1 which is (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid ethyl ester hydrochloride or a pharmaceutically acceptable salt thereof.

31. The compound according to claim 1 which is (RS)- and (SR)-(4-carbamimidoyl-phenylamino)-{5-ethoxy-2-fluoro-3-[(RS)-1-(2-hydroxy-ethyl)-piperidin-3-yloxy]-phenyl}-acetic acid or a pharmaceutically acceptable salt thereof.

32. The compound according to claim 1 which is (RS)-(4-carbamimidoyl-phenylamino)-[5-ethoxy-2-fluoro-3-(piperidin-4-yloxy)-phenyl]-acetic acid ethyl ester hydrochloride or a pharmaceutically acceptable salt thereof.

33. The compound according to claim 1 which is (RS)-(4-carbamimidoyl-phenylamino)-[5-ethoxy-2-fluoro-3-(piperidin-4-yloxy)-phenyl]-acetic acid or a pharmaceutically acceptable salt thereof.

34. The compound according to claim 1 which is (RS)-(4-carbamimidoyl-phenylamino)-[5-ethoxy-2-fluoro-3-(1-methyl-piperidin-4-yloxy)-phenyl]-acetic acid ethyl ester hydrochloride(1:2) or a pharmaceutically acceptable salt thereof.

35. The compound according to claim 1 which is (RS)-(4-carbamimidoyl-phenylamino)-[5-ethoxy-2-fluoro-3-(1- methyl-piperidin-4-yloxy)-phenyl]-acetic acid or a pharmaceutically acceptable salt thereof.

36. The compound according to claim 1 which is (S)-(4-carbamimidoyl-phenylamino)-[5-ethoxy-2-fluoro-3-(1-methyl-piperidin-4-yloxy)-phenyl]-acetic acid or a pharmaceutically acceptable salt thereof.

37. The compound according to claim 1, wherein the compound is of the formula

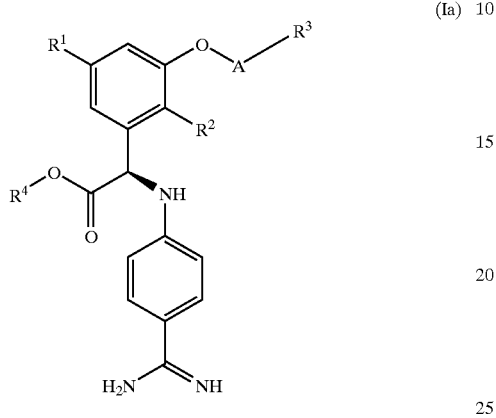

(Ia)

wherein $R^1$, $R^2$, $R^3$, $R^4$, A, and n have the significances given in claim 1.

38. The compound according to claim 37 which is (R)-(4-carbamimidoyl-phenylamino)-[5-ethoxy-2-fluoro-3-(1-methyl-piperidin-4-yloxy)-phenyl]-acetic acid or a pharmaceutically acceptable salt thereof.

39. A compound of the formula:

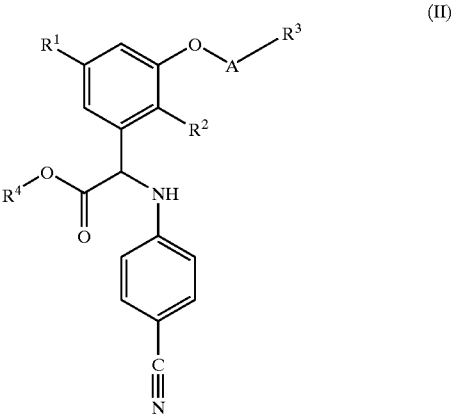

(II)

wherein
  $R^1$ is lower-alkoxy;
  $R^2$ is halogen;
  $R^3$ is piperidinyl or piperidinyl substituted with lower-alkyl, hydroxy-lower-alkyl, carboxy-lower-alkyl or lower-alkoxy-carbonyl-lower-alkyl;
  $R^4$ is hydrogen or lower-alkyl;
  A is —$(CH_2)_n$— or —$(CH_2)_n$— which is substituted with lower-alkyl; and
  n is 0 to 3;
  or a pharmaceutically acceptable salt thereof.

* * * * *

UNITED STATES PATENT AND TRADEMARK OFFICE
CERTIFICATE OF CORRECTION

PATENT NO. : 6,642,386 B2
DATED : November 4, 2003
INVENTOR(S) : Alig et al.

It is certified that error appears in the above-identified patent and that said Letters Patent is hereby corrected as shown below:

Column 24,
Line 24, delete "The compound according to claim 1 which is (RS)-(4-carbamimidoyl-phenylamino)-{5-ethoxy-2-fluoro-3-[1-(2-hydroxy-ethyl)-piperidin-4-yloxy]-phenyl} acid ethyl ester hydrochloride or a pharmaceutically acceptable salt thereof." and insert -- The compound according to claim 1 which is (RS)-(4-carbamimidoyl-phenylamino)-{5-ethoxy-2-fluoro-3-[1-(2-hydroxy-ethyl)-piperidin-4-yloxy]-phenyl}-acetic acid ethyl ester hydrochloride or a pharmaceutically acceptable salt thereof. --

Signed and Sealed this

Twenty-second Day of June, 2004

JON W. DUDAS
*Acting Director of the United States Patent and Trademark Office*